US012599748B2

(12) United States Patent
Howell et al.

(10) Patent No.: US 12,599,748 B2
(45) Date of Patent: Apr. 14, 2026

(54) CATHETER TIPS FOR RAPIDLY INSERTABLE CENTRAL CATHETERS AND METHODS THEREOF

(71) Applicant: Bard Access Systems, Inc., Salt Lake City, UT (US)

(72) Inventors: Glade H. Howell, Draper, UT (US); Juan Sepulveda, Centerville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 584 days.

(21) Appl. No.: 18/076,169

(22) Filed: Dec. 6, 2022

(65) Prior Publication Data

US 2024/0181210 A1     Jun. 6, 2024

(51) Int. Cl.
*A61M 25/00*          (2006.01)
(52) U.S. Cl.
CPC ...... *A61M 25/0068* (2013.01); *A61M 25/008* (2013.01)
(58) Field of Classification Search
CPC .......... A61M 25/0023; A61M 25/0068; A61M 25/0041; A61M 25/0043
See application file for complete search history.

(56) References Cited

U.S. PATENT DOCUMENTS

| | | | |
|---|---|---|---|
| 1,013,691 A | 1/1912 | Shields | |
| 1,906,678 A | 5/1933 | Wappler | |
| 3,225,762 A | 12/1965 | Guttman | |
| 3,710,781 A | 1/1973 | Huthcins, IV et al. | |

| | | | |
|---|---|---|---|
| 3,890,976 A | 6/1975 | Bazell et al. | |
| 4,205,675 A | 6/1980 | Vaillancourt | |
| 4,270,535 A | 6/1981 | Bogue et al. | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |

(Continued)

FOREIGN PATENT DOCUMENTS

| | | |
|---|---|---|
| EP | 0730880 A1 | 9/1996 |
| EP | 2061385 A1 | 5/2009 |

(Continued)

OTHER PUBLICATIONS

PCT/US2020/048583 filed Aug. 28, 2020 International Search Report and Written Opinion dated Nov. 13, 2020.

(Continued)

*Primary Examiner* — Imani N Hayman
(74) *Attorney, Agent, or Firm* — Rutan & Tucker LLP

(57)          ABSTRACT

A rapidly inserted central catheter can include a catheter tube, a catheter hub, and one or more extension legs. The catheter tube can include a single-piece catheter tip coupled to a distal end portion of the catheter tube having a first section, a second section, and a third section. The first section of the catheter tip can have a uniform taper over an outer diameter thereof for dilating tissue around a needle tract from a size commensurate with an outer diameter of a needle shaft to a size commensurate with an outer diameter of the second section of the catheter tip. The third section of the catheter tip can have a non-uniform taper over an outer diameter thereof for dilating the tissue from the size commensurate with the outer diameter of the second section of the catheter tip to a size commensurate with an outer diameter of the catheter tube.

16 Claims, 6 Drawing Sheets

(56) References Cited

U.S. PATENT DOCUMENTS

| | | | |
|---|---|---|---|
| 4,661,300 A | 4/1987 | Daugherty |
| 5,004,455 A | 4/1991 | Greenwood et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,120,317 A | 6/1992 | Luther |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton et al. |
| 5,306,247 A | 4/1994 | Pfenninger |
| 5,328,472 A | 7/1994 | Steinke et al. |
| 5,350,358 A | 9/1994 | Martin |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,489,271 A | 2/1996 | Andersen |
| 5,573,520 A | 11/1996 | Schwartz et al. |
| 5,645,528 A | 7/1997 | Thome |
| 5,683,370 A | 11/1997 | Luther et al. |
| 5,690,613 A | 11/1997 | Verbeek |
| 5,718,678 A | 2/1998 | Fleming, III |
| 5,772,636 A | 6/1998 | Brimhall et al. |
| 5,810,789 A | 9/1998 | Powers et al. |
| 5,885,251 A | 3/1999 | Luther |
| 5,908,409 A | 6/1999 | Rinehart et al. |
| 5,919,164 A | 7/1999 | Andersen |
| 5,947,940 A | 9/1999 | Beisel |
| 5,957,893 A | 9/1999 | Luther et al. |
| 6,206,849 B1 | 3/2001 | Martin et al. |
| 6,332,877 B1 | 12/2001 | Michels |
| 6,475,187 B1 | 11/2002 | Gerberding |
| 6,606,515 B1 | 8/2003 | Windheuser et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,985,204 B2 | 7/2011 | Katoh et al. |
| 8,073,517 B1 | 12/2011 | Burchman |
| 8,105,286 B2 | 1/2012 | Anderson et al. |

| | | | |
|---|---|---|---|
| 8,192,402 B2 | 6/2012 | Anderson et al. |
| 8,202,251 B2 | 6/2012 | Bierman et al. |
| 8,206,356 B2 | 6/2012 | Katoh et al. |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,950,139 B2 | 4/2018 | Blanchard et al. |
| 9,981,113 B2 | 5/2018 | Bierman |
| 10,010,312 B2 | 7/2018 | Tegels |
| 10,065,020 B2 | 9/2018 | Gaur |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 2001/0044594 A1 | 11/2001 | Martin et al. |
| 2002/0040231 A1 | 4/2002 | Wysoki |
| 2002/0107506 A1 | 8/2002 | McGuckin et al. |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0116901 A1 | 6/2004 | Appling |
| 2004/0193093 A1 | 9/2004 | Desmond |
| 2004/0230178 A1 | 11/2004 | Wu |
| 2005/0004554 A1 | 1/2005 | Osborne |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2008/0039796 A1 | 2/2008 | Nakajima |
| 2008/0045894 A1 | 2/2008 | Perchik et al. |
| 2008/0125744 A1 | 5/2008 | Treacy |
| 2008/0125748 A1 | 5/2008 | Patel |
| 2008/0262430 A1 | 10/2008 | Anderson et al. |
| 2008/0262431 A1 | 10/2008 | Anderson et al. |
| 2008/0294111 A1 | 11/2008 | Tal et al. |

(56) References Cited

U.S. PATENT DOCUMENTS

| | | |
|---|---|---|
| 2008/0312578 A1 | 12/2008 | DeFonzo et al. |
| 2009/0093670 A1 | 4/2009 | Annest et al. |
| 2009/0221961 A1 | 9/2009 | Tal et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0209221 A1 | 8/2012 | Patterson et al. |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0012924 A1 | 1/2013 | Davis et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094741 A1 | 4/2014 | Bellisario et al. |
| 2014/0100552 A1 | 4/2014 | Gallacher et al. |
| 2014/0155863 A1 | 6/2014 | Walker et al. |
| 2014/0180255 A1 | 6/2014 | LeBlanc et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0220786 A1 | 8/2016 | Mitchell et al. |
| 2016/0220795 A1 | 8/2016 | Korkuch et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035989 A1 | 2/2017 | Gilman |
| 2017/0035990 A1 | 2/2017 | Swift |
| 2017/0072165 A1 | 3/2017 | Lim et al. |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0333681 A1 | 11/2017 | Di Caprio et al. |
| 2017/0361070 A1 | 12/2017 | Hivert |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0193042 A1 | 7/2018 | Wilson et al. |
| 2018/0296799 A1 | 10/2018 | Horst et al. |
| 2018/0296804 A1 | 10/2018 | Bierman |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2021/0069471 A1 | 3/2021 | Howell |
| 2021/0121661 A1 | 4/2021 | Howell |
| 2021/0121667 A1 | 4/2021 | Howell |
| 2021/0187245 A1 | 6/2021 | Ishida |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0040447 A1 | 2/2022 | Mewissen |
| 2023/0126869 A1 | 4/2023 | Sepulveda et al. |
| 2023/0132903 A1 | 5/2023 | Sepulveda et al. |
| 2023/0233796 A1 | 7/2023 | Howell |
| 2023/0233800 A1 | 7/2023 | Howell et al. |
| 2024/0091501 A1 | 3/2024 | Howell |
| 2024/0198042 A1 | 6/2024 | Sepulveda |

FOREIGN PATENT DOCUMENTS

| | | |
|---|---|---|
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3093038 B1 | 5/2019 |
| EP | 2260897 B1 | 9/2019 |
| ES | 2303546 T3 | 8/2008 |
| GB | 1273547 A | 5/1972 |
| WO | 9421315 A1 | 9/1994 |
| WO | 95/32009 A2 | 11/1995 |
| WO | 9844979 A1 | 10/1998 |
| WO | 9853871 A1 | 12/1998 |
| WO | 9912600 A1 | 3/1999 |
| WO | 99/26681 A1 | 6/1999 |
| WO | 2003008020 A1 | 1/2003 |
| WO | 2003057272 A2 | 7/2003 |
| WO | 2003066125 A2 | 8/2003 |
| WO | 2004037331 A1 | 5/2004 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008131289 A2 | 10/2008 |
| WO | 2008131300 A2 | 10/2008 |
| WO | 2009114833 A1 | 9/2009 |
| WO | 2009114837 A2 | 9/2009 |
| WO | 2010048449 A2 | 4/2010 |
| WO | 2010056906 A2 | 5/2010 |
| WO | 2010083467 A2 | 7/2010 |
| WO | 2010132608 A2 | 11/2010 |
| WO | 2011081859 A2 | 7/2011 |
| WO | 2011097639 A2 | 8/2011 |
| WO | 2011146764 A1 | 11/2011 |
| WO | 2012068162 A2 | 5/2012 |

(56)    References Cited

FOREIGN PATENT DOCUMENTS

| WO | 2012068166 | A2 | 5/2012 |
|----|------------|----|--------|
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021062023 | A1 | 4/2021 |
| WO | 2021077103 | A1 | 4/2021 |
| WO | 2021081205 | A1 | 4/2021 |
| WO | 2021086793 | A1 | 5/2021 |
| WO | 2023069553 | A2 | 4/2023 |
| WO | 2023081314 | A1 | 5/2023 |
| WO | 2023141112 | A1 | 7/2023 |
| WO | 2023146773 | A3 | 9/2023 |
| WO | 2024123925 | A2 | 6/2024 |
| WO | 2024129815 | A1 | 6/2024 |

OTHER PUBLICATIONS

PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/006,553, filed Aug. 28, 2020 Final Office Action dated Sep. 28, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
PCT/US2023/082753 filed Dec. 6, 2023 International Search Report and Written Opinion dated May 29, 2024.
U.S. Appl. No. 17/363,500, filed Jun. 30, 2021 Non-Final Office Action dated Sep. 23, 2024.
U.S. Appl. No. 17/363,500, filed Jun. 30, 2021 Restriction Requirement dated Jul. 16, 2024.
EP 20862936.0 filed Mar. 28, 2022 Extended European Search Report dated Sep. 19, 2023.
PCT/US2023/010971 filed Jan. 17, 2023 International Search Report and Written Opinion dated Jul. 28, 2023.
U.S. Appl. No. 17/006,553, filed Aug. 28, 2020 Notice of Allowance dated Sep. 11, 2023.
Yamada, T. et al., "Selective Hemi-Portocaval Shunt Based on Portal Vein Pressure for Small-for-Size Graft in Adult Living Donor Liver Transplantation." American Journal of Transplantation, Blackwell Munksgaard, DK, vol. 8, No. 4, Feb. 5, 2008 [Feb. 5, 2008] pp. 847-853.
PCT/US2022/047179 filed Oct. 19, 2022 International Preliminary Report on Patentability dated Apr. 23, 2024.
PCT/US2023/083764 filed Dec. 13, 2023 International Search Report and Written Opinion dated Apr. 22, 2024.
PCT/US2022/047179 filed Oct. 19, 2022 International Search Report and Written Opinion dated Apr. 18, 2023.
PCT/US2022/048881 filed Nov. 3, 2022 International Search Report and Written Opinion dated Mar. 31, 2023.
PCT/US2023/010972 filed Jan. 17, 2023 International Search Report and Written Opinion dated May 30, 2023.
U.S. Appl. No. 17/006,553, filed Aug. 28, 2020 Non-Final Office Action dated Jun. 26, 2023.
U.S. Appl. No. 17/363,500, filed Jun. 30, 2021 Final Office Action dated Feb. 20, 2025.
U.S. Appl. No. 17/363,500, filed Jun. 30, 2021 Non-Final Office Action dated Sep. 4, 2025.
U.S. Appl. No. 17/969,626, filed Oct. 19, 2022 Non-Final Office Action dated Sep. 25, 2025.
U.S. Appl. No. 18/081,480, filed Dec. 14, 2022 Non-Final Office Action dated Sep. 17, 2025.

$$\ell_3 > \ell_2 > \ell_1$$

CATHETER TIPS FOR RAPIDLY INSERTABLE CENTRAL CATHETERS AND METHODS THEREOF

BACKGROUND

An acute central venous catheter ("ACVC") is typically inserted using the Seldinger technique. In accordance with the Seldinger technique, a needle tract to a blood-vessel lumen is dilated with a separate dilator prior to advancing the ACVC over an access guidewire into the blood-vessel lumen for subsequent placement. It would be advantageous if clinicians could skip dilation of the blood-vessel lumen with the separate dilator. However, current ACVCs have relatively blunt catheter tips making it difficult to do so.

Disclosed herein are catheter tips for rapidly insertable central catheter ("RICCs") and methods thereof that address the foregoing.

SUMMARY

Disclosed herein is a RICC including, in some embodiments, a catheter tube, a single-piece catheter tip coupled to a distal end portion of the catheter tube, a catheter hub coupled to a proximal portion of the catheter tube, and one or more extension legs with each extension leg of the one-or-more extension legs coupled to the catheter hub by a distal portion thereof. The catheter tube includes a catheter-tube portion of a primary lumen of the RICC, which primary lumen has an inner diameter. The catheter tip has a first section, a second section, and a third section. The first section of the catheter tip has a uniform taper over an outer diameter of the first section for dilating tissue around a needle tract from a size commensurate with an outer diameter of a needle shaft of an introducer needle to a size commensurate with an outer diameter of the second section of the catheter tip. The third section of the catheter tip has a non-uniform taper over an outer diameter of the third section for dilating the tissue from the size commensurate with the outer diameter of the second section of the catheter tip to a size commensurate with an outer diameter of the catheter tube.

In some embodiments, each successive transverse cross section of the first section of the catheter tip approximates a larger concentric annulus in a proximal direction along the first section of the catheter tip. In addition, each successive transverse cross section of the first section of the catheter tip approximates a smaller concentric annulus in a distal direction along the first section of the catheter tip. Each concentric annulus of the foregoing larger and smaller concentric annuli is defined by the outer diameter of the first section of the catheter tip and the inner diameter of the catheter-tube portion of the primary lumen of the RICC, thereby providing the uniform taper of the first section of the catheter tip.

In some embodiments, each successive transverse cross section of the third section of the catheter tip approximates a larger eccentric annulus in a proximal direction along the third section of the catheter tip. In addition, each successive transverse cross section of the third section of the catheter tip approximates a smaller eccentric annulus in a distal direction along the third section of the catheter tip. Each eccentric annulus of the foregoing larger and smaller eccentric annuli is defined by the outer diameter of the third section of the catheter tip and the inner diameter of the catheter-tube portion of the primary lumen of the RICC, thereby providing the non-uniform taper of the third section of the catheter tip.

In some embodiments, the second section of the catheter tip does not have a taper. The outer diameter of the second section of the catheter tip is consistent along the second section of the catheter tip.

In some embodiments, the uniform taper of the first section of the catheter tip has a constant first taper angle. In addition, the non-uniform taper of the third section of the catheter tip has a variable third taper angle. The first taper angle is greater than the third taper angle at a greatest taper angle of the third taper angle.

In some embodiments, the second section of the catheter tip has a uniform taper for dilating the tissue from a size commensurate with the outer diameter of the first section of the catheter tip to the size commensurate with the outer diameter of the third section of the catheter tip.

In some embodiments, each successive transverse cross section of the second section of the catheter tip approximates a larger concentric annulus in a proximal direction along the second section of the catheter tip. In addition, each successive transverse cross section of the second section of the catheter tip approximates a smaller concentric annulus in a distal direction along the second section of the catheter tip. Each concentric annulus of the foregoing larger and smaller concentric annuli is defined by the outer diameter of the second section of the catheter tip and the inner diameter of the catheter-tube portion of the primary lumen of the RICC, thereby providing the uniform taper of the second section of the catheter tip.

In some embodiments, the uniform taper of the first section of the catheter tip has a constant first taper angle. In addition, the uniform taper of the second section of the catheter tip has a constant second taper angle. Lastly, the non-uniform taper of the third section of the catheter tip has a variable third taper angle. The first taper angle is greater than the third taper angle at a greatest taper angle of the third taper angle. That, and the third taper angle is greater than the second taper angle at the greatest taper angle of the third taper angle.

In some embodiments, the second section of the catheter tip is about 4.0 to 5.0 times longer than the first section of the catheter tip.

In some embodiments, the third section of the catheter tip is about 4.5 to 7.5 times longer than the second section of the catheter tip.

In some embodiments, the catheter tip is of a first polymeric material. In addition, the catheter tube is of a second, softer polymeric material than the first polymeric material.

In some embodiments, the first polymeric material is sufficiently stiff to prevent the catheter tip from collapsing, buckling, or otherwise appreciably deforming when a distal portion of the RICC is advanced into a blood-vessel lumen of a patient. In addition, the first polymeric material is sufficiently pliable to prevent trauma to the blood-vessel lumen when the distal portion of the RICC is advanced farther into the blood-vessel lumen.

In some embodiments, the RICC includes a set of three lumens including the primary lumen, a secondary lumen, and a tertiary lumen. The set of three lumens is formed of fluidly connected portions of at least three catheter-tube lumens, three catheter-hub lumens, and three extension-leg lumens. The secondary and tertiary lumens terminate in the distal end portion of the catheter tube by at least some infill of melted polymeric material of the first polymeric material.

In some embodiments, the primary lumen has a primary-lumen aperture in a distal end of the catheter tip. In addition, the secondary lumen has a secondary-lumen aperture in a side of the distal portion of the catheter tube. Lastly, the tertiary lumen has a tertiary-lumen aperture in the side of the distal end portion of the catheter tube but proximal of the secondary-lumen aperture.

Also disclosed herein is a method for forming a catheter tip of a RICC. The method includes, in some embodiments, a workpiece-inserting step, a die-heating step, and a mandrel-thrusting step. The workpiece-inserting step includes inserting a mandrel-mounted catheter tube as a workpiece into a cavity of a radiofrequency ("RF")-welding die. A distal end of a mandrel of the mandrel-mounted catheter tube remains short of an end of the cavity after the inserting of the mandrel-mounted catheter tube therein. The die-heating step includes heating the RF-welding die to melt a first polymeric material in the cavity of the RF-welding die. During the heating of the RF-welding die, molten polymeric material of the first polymeric material is allowed to conform to the cavity around the mandrel to form, in a single piece, a nascent catheter tip coupled to a distal end portion of the catheter tube. The mandrel-thrusting step includes thrusting the distal end of the mandrel into the end of the cavity of the RF-welding die when the molten polymeric material exudes through an exit hole in the end of the cavity. Excess polymeric material is cut from a distal end of the nascent catheter tip with the thrusting of the distal end of the mandrel into the end of the cavity to form the catheter tip coupled to the distal end portion of the catheter tube.

In some embodiments, the method further includes a catheter-tube obtaining step. The catheter-tube obtaining step includes either sourcing or extruding the catheter tube of a second, softer polymeric material than the first polymer material. The catheter tube includes a primary catheter-tube lumen, a secondary catheter-tube lumen, and a tertiary catheter-tube lumen corresponding to catheter-tube portions of a primary lumen, a secondary lumen, and a tertiary lumen of the RICC, respectively.

In some embodiments, the method further includes a polymeric plug-inserting step. The polymeric plug-inserting step includes at least partially inserting a polymeric plug of the first polymeric material into each lumen of the secondary and tertiary catheter-tube lumens for melting the first polymeric material in the cavity of the RF-welding die while heating the RF-welding die in the die-heating step.

In some embodiments, the method further includes a workpiece-removing step and a mandrel-removing step. The workpiece-removing step includes removing a mandrel-mounted tipped catheter tube as the workpiece from the cavity of the RF-welding die. The mandrel-removing step includes removing the mandrel from the mandrel-mounted tipped catheter tube to provide a tipped catheter tube. A remainder of the polymeric plug in the secondary and tertiary catheter-tube lumens, melted polymeric material of the first polymeric material in the secondary and tertiary catheter-tube lumens, or a combination thereof in the secondary and tertiary catheter-tube lumens terminate the secondary and tertiary catheter-tube lumens as infill upon cooling the mandrel-mounted tipped catheter tube or the tipped catheter tube.

In some embodiments, the catheter tip has a first section, a second section, and a third section. The first section of the catheter tip has a uniform taper over an outer diameter of the first section for dilating tissue around a needle tract from a size commensurate with an outer diameter of a needle shaft of an introducer needle to a size commensurate with an outer diameter of the second section of the catheter tip. The third section of the catheter tip has a non-uniform taper over an outer diameter of the third section for dilating the tissue from the size commensurate with the outer diameter of the second section of the catheter tip to a size commensurate with an outer diameter of the catheter tube.

In some embodiments, the second section of the catheter tip does not have a taper. The outer diameter of the second section of the catheter tip is consistent along the second section of the catheter tip.

In some embodiments, the second section of the catheter tip has a uniform taper for dilating the tissue from a size commensurate with the outer diameter of the first section of the catheter tip to the size commensurate with the outer diameter of the third section of the catheter tip.

In some embodiments, the first polymeric material of the catheter tip is sufficiently stiff to prevent the catheter tip from collapsing, buckling, or otherwise appreciably deforming when a distal portion of the RICC is advanced into a blood-vessel lumen of a patient. In addition, the first polymeric material of the catheter tip is sufficiently pliable to prevent trauma to the blood-vessel lumen when the distal portion of the RICC is advanced farther into the blood-vessel lumen.

Also disclosed herein is a method of placing a RICC. The method includes, in some embodiments, an initial RICC-advancing step and a dilating step. The initial RICC-advancing step includes advancing a distal portion of the RICC over an access guidewire into a blood-vessel lumen of a patient. The distal portion of the RICC includes a single-piece catheter tip of a first polymeric material having a first section, a second section, and a third section coupled to a distal end portion of a catheter tube of a second polymeric material. The first polymeric material of the catheter tip is sufficiently stiff to prevent the catheter tip from collapsing, buckling, or otherwise appreciably deforming while advancing the distal portion of the RICC over the access guidewire into the blood-vessel lumen. The dilating step includes dilating tissue around a needle tract leading to the blood-vessel lumen while advancing the distal portion of the RICC into the blood-vessel lumen in the initial RICC-advancing step. The first section of the catheter tip has a uniform taper over an outer diameter of the first section for dilating the tissue from a size commensurate with an outer diameter of a needle shaft of an introducer needle used to establish the needle tract to a size commensurate with an outer diameter of the second section of the catheter tip. The third section of the catheter tip has a non-uniform taper over an outer diameter of the third section for dilating the tissue from the size commensurate with the outer diameter of the second section of the catheter tip to a size commensurate with an outer diameter of the catheter tube.

In some embodiments, the method further includes a guidewire-exchanging step, a maneuver guidewire-advancing step, a subsequent RICC-advancing step, and a maneuver guidewire-withdrawing step. The guidewire-exchanging step includes exchanging the access guidewire with a maneuver guidewire. The maneuver guidewire-advancing step includes advancing a distal portion of the maneuver guidewire farther into the blood-vessel lumen to a lower ⅓ of a superior vena cava ("SVC") of a heart of the patient. The subsequent RICC-advancing step includes advancing the distal portion of the RICC farther into the blood-vessel lumen over the maneuver guidewire to the lower ⅓ of the SVC. The first polymeric material is also sufficiently pliable to prevent trauma to the blood-vessel lumen while advancing the distal portion of the RICC over the maneuver guidewire farther into the blood-vessel lumen. The maneuver guidewire-withdrawing step includes withdrawing the maneuver guidewire leaving the catheter tube in place in the lower ⅓ of the SVC.

In some embodiments, the second section of the catheter tip does not have a taper. The outer diameter of the second section of the catheter tip is consistent along the second section of the catheter tip.

In some embodiments, the second section of the catheter tip has a uniform taper for dilating the tissue from a size commensurate with the outer diameter of the first section of the catheter tip to the size commensurate with the outer diameter of the third section of the catheter tip.

These and other features of the concepts provided herein will become more apparent to those of skill in the art in view of the accompanying drawings and following description, which describe particular embodiments of such concepts in greater detail.

DRAWINGS

DESCRIPTION

Figure 1:
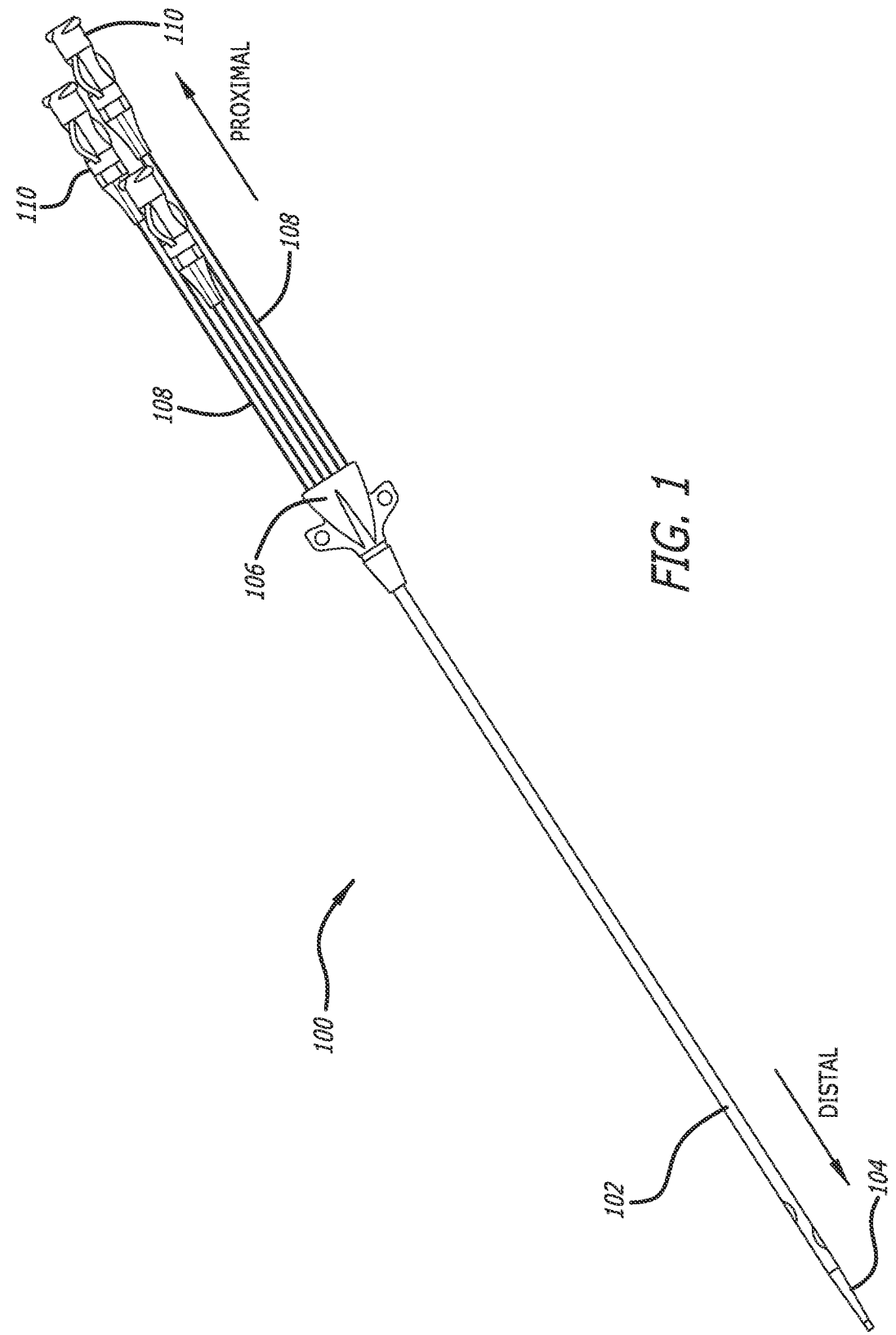
FIG. 1 illustrates a RICC in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

"Proximal" refers to a portion, section, piece, element, or the like of a medical device intended to be near or relatively nearer to a clinician when the medical device is used on a patient. For example, a "proximal portion" or "proximal section" of the medical device includes a portion or section of the medical device intended to be near the clinician when the medical device is used on the patient. Likewise, a "proximal length" of the medical device includes a length of the medical device intended to be near the clinician when the medical device is used on the patient. A "proximal end" of the medical device is an end of the medical device intended to be near the clinician when the medical device is used on the patient. The proximal portion, the proximal section, or the proximal length of the medical device need not include the proximal end of the medical device. Indeed, the proximal portion, the proximal section, or the proximal length of the medical device can be short of the proximal end of the medical device. However, the proximal portion, the proximal section, or the proximal length of the medical device can include the proximal end of the medical device. Should context not suggest the proximal portion, the proximal section, or the proximal length of the medical device includes the proximal end of the medical device, or if it is deemed expedient in the following description, "proximal portion," "proximal section," or "proximal length" can be modified to indicate such a portion, section, or length includes an end portion, an end section, or an end length of the medical device for a "proximal end portion," a "proximal end section," or a "proximal end length" of the medical device, respectively.

"Distal" refers to a portion, section, piece, element, or the like of a medical device intended to be near, relatively nearer, or even in a patient when the medical device is used on the patient. For example, a "distal portion" or "distal section" of the medical device includes a portion or section of the medical device intended to be near, relatively nearer, or even in the patient when the medical device is used on the patient. Likewise, a "distal length" of the medical device includes a length of the medical device intended to be near, relatively nearer, or even in the patient when the medical device is used on the patient. A "distal end" of the medical device is an end of the medical device intended to be near, relatively nearer, or even in the patient when the medical device is used on the patient. The distal portion, the distal section, or the distal length of the medical device need not include the distal end of the medical device. Indeed, the distal portion, the distal section, or the distal length of the medical device can be short of the distal end of the medical device. However, the distal portion, the distal section, or the distal length of the medical device can include the distal end of the medical device. Should context not suggest the distal portion, the distal section, or the distal length of the medical device includes the distal end of the medical device, or if it is deemed expedient in the following description, "distal portion," "distal section," or "distal length" can be modified to indicate such a portion, section, or length includes an end portion, an end section, or an end length of the medical device for a "distal end portion," a "distal end section," or a "distal end length" of the medical device, respectively.

Unless defined otherwise, all technical and scientific terms used herein have the same meaning as commonly understood by those of ordinary skill in the art.

Again, an ACVC is typically inserted using the Seldinger technique. In accordance with the Seldinger technique, a needle tract to a blood-vessel lumen is dilated with a separate dilator prior to advancing the ACVC over an access guidewire into the blood-vessel lumen for subsequent placement. It would be advantageous if clinicians could skip dilation of the blood-vessel lumen with the separate dilator. However, current ACVCs have relatively blunt catheter tips making it difficult to do so.

Disclosed herein are catheter tips for RICCs and methods thereof that address the foregoing.

RICCs

FIG. 1 illustrates a RICC 100 in accordance with some embodiments.

As shown, the RICC 100 can include a catheter tube 102 having a single-piece catheter tip 104 coupled thereto, a catheter hub 106, and one or more extension legs 108. The catheter tip 104 can be coupled to a distal end portion of the catheter tube 102, and the catheter hub 106 can be coupled to a proximal end portion of the catheter tube 102. Each extension leg of the one-or-more extension legs 108 can be coupled to the catheter hub 106 by a distal end portion thereof. In addition, one or more extension-leg connectors 110 (e.g., Luer connectors) can be coupled to the one-or-more extension legs 108 for connecting one or more other medical devices, respectively.

The RICC 100 can be a monoluminal RICC or a multi-luminal RICC (e.g., a diluminal RICC, a triluminal RICC, a tetraluminal RICC, a pentaluminal RICC, a hexaluminal RICC, etc.). For example, the RICC 100 can be a triluminal RICC including a set of three lumens as provided in FIG. 1. (See also FIG. 6.) The set of three lumens can include a primary lumen 112 having an inner diameter (e.g., any of $d_{Ai}$, $d_{Bi}$, or $d_{Ci}$ of FIG. 8 or $d_{Di}$, $d_{Ei}$, or $d_{Fi}$ of FIG. 9), a secondary lumen 114, and a tertiary lumen 116. Each lumen of the primary lumen 112, the secondary lumen 114, and the tertiary lumen 116 of the RICC 100 can be formed of at least three fluidly connected luminal portions, namely those of a catheter-tube lumen, a catheter-hub lumen, and an extension-leg lumen of three catheter-tube lumens 118, 120, and 122, three catheter-hub lumens, and three extension-leg lumens in the RICC 100. For instance, the primary lumen 112 of the RICC 100 can be formed of a primary catheter-tube lumen 118, a primary catheter-hub lumen, and a primary extension-leg lumen; however, the primary lumen 112 of the RICC 100 can further include a fluidly connected catheter-tip lumen 124 of the catheter tip 104 as well. Further, the secondary lumen 114 of the RICC 100 can be formed of a secondary catheter-tube lumen 120, a secondary catheter-hub lumen, and a secondary extension-leg lumen. Lastly, the tertiary lumen 116 of the RICC 100 can be formed of a tertiary catheter-tube lumen 122, a tertiary catheter-hub lumen, and a tertiary extension-leg lumen. The primary lumen 112 can have a primary-lumen aperture 126 in a distal end of the catheter tip 104, which corresponds to a distal end of the RICC 100. The secondary lumen 114 can have a secondary-lumen aperture 128 in a side of the distal portion of the catheter tube 102. The tertiary lumen 116 can have a tertiary-lumen aperture 130 in the side of the distal portion of the catheter tube 102 proximal of the secondary-lumen aperture 128. Like the secondary and tertiary lumens 114 and 116, each additional lumen can have a corresponding lumen aperture in the side of the distal portion of the catheter tube 102 proximal of its predecessor.

Catheter Tips

Figures 2, 3:
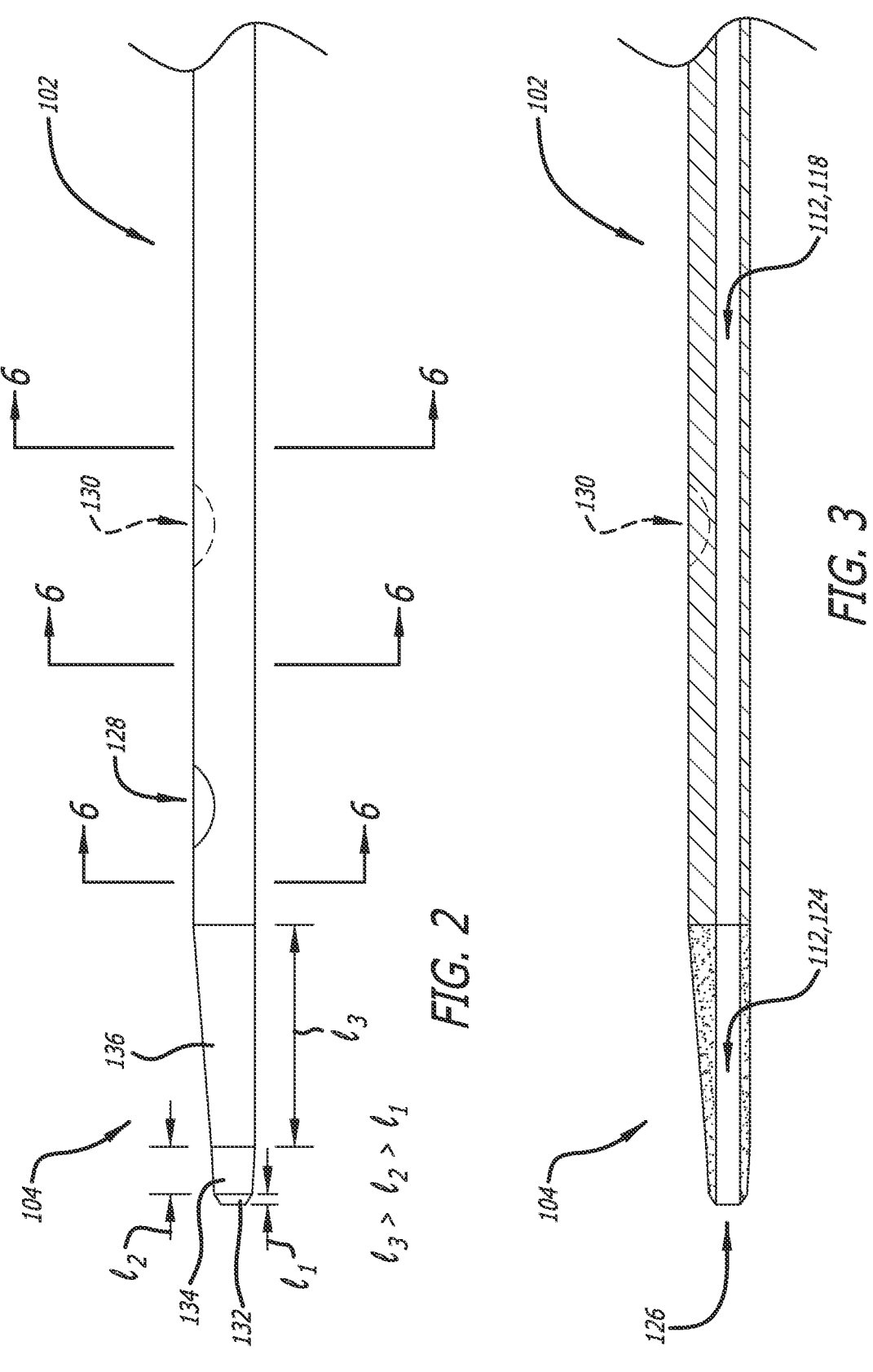
FIG. 2 illustrates a detailed view of a catheter tip coupled to a distal portion of a catheter tube of the RICC in accordance with some embodiments.
FIG. 3 illustrates a longitudinal cross section of the catheter tip and catheter tube of FIG. 2 in accordance with some embodiments.
Figures 4, 5:
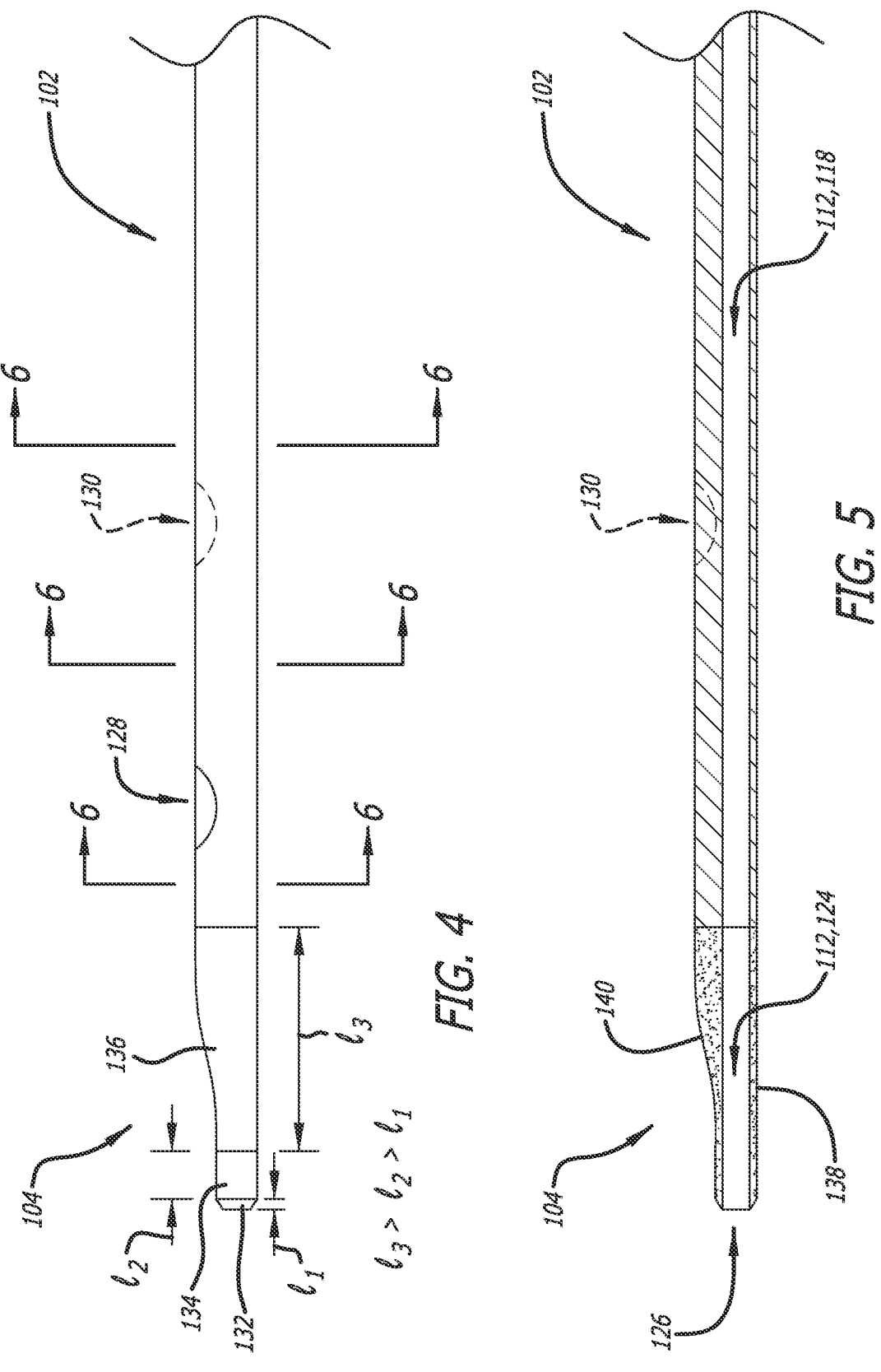
FIG. 4 illustrates a detailed view of another catheter tip coupled to the distal portion of the catheter tube in accordance with some embodiments.
FIG. 5 illustrates a longitudinal cross section of the catheter tip and catheter tube of FIG. 4 in accordance with some embodiments.
Figures 6, 7:
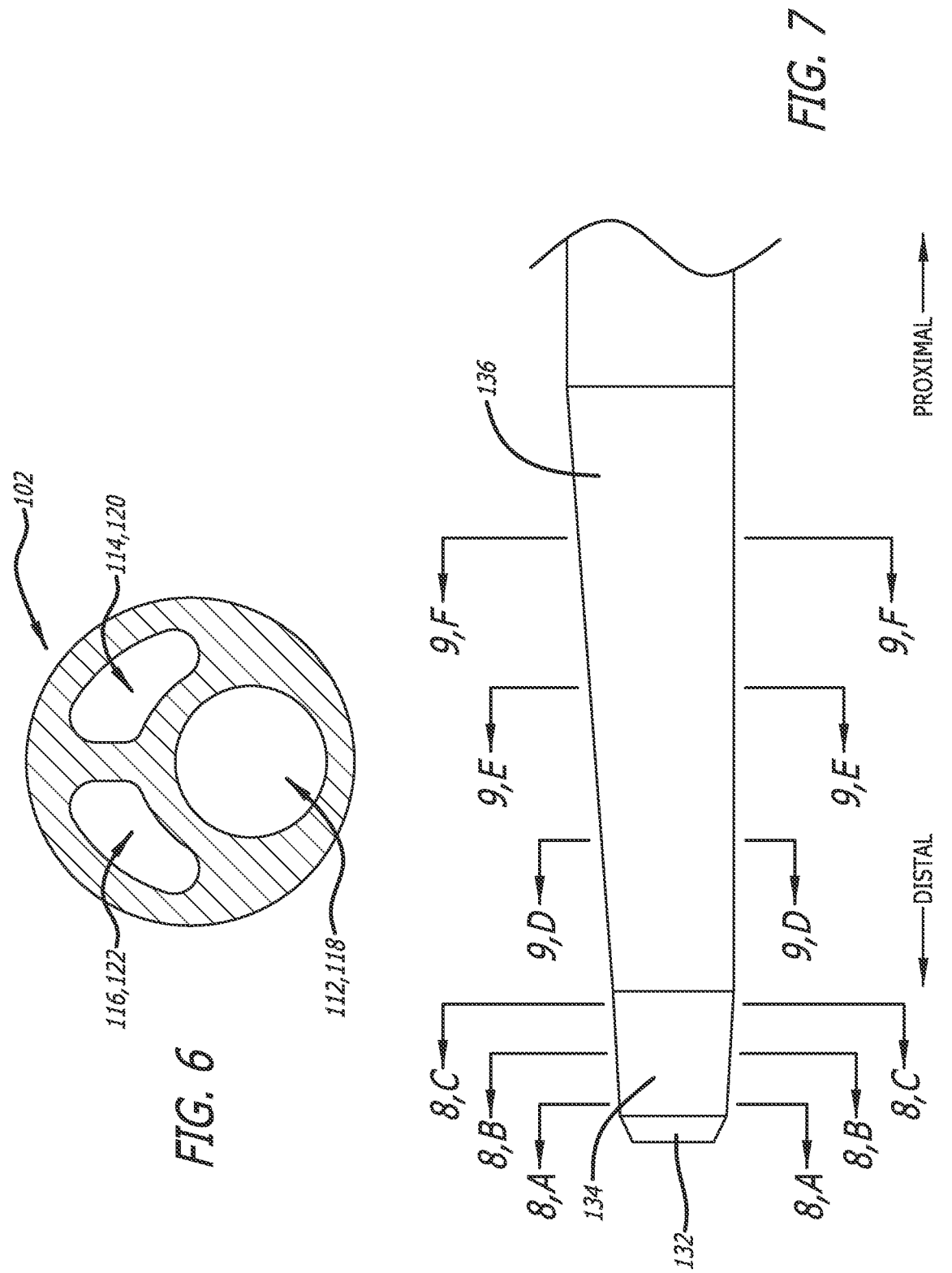
FIG. 6 illustrates a transverse cross section of the distal portion of the catheter tube in accordance with some embodiments.
FIG. 7 illustrates a detailed view of the catheter tip of FIG. 2 in accordance with some embodiments.

FIGS. 2 and 4 illustrate detailed views of the catheter tube 102 with the catheter tip 104 coupled thereto in accordance with some embodiments. FIGS. 3 and 5 illustrate longitudinal cross sections of the catheter tube 102 with the catheter tip 104 of FIGS. 2 and 4, respectively, in accordance with some embodiments. FIG. 6 illustrates a transverse cross section of the distal portion of the catheter tube 102 in accordance with some embodiments.

As shown, the catheter tube 102 can include one or more catheter-tube lumens such as the three catheter-tube lumens 118, 120, and 122 set forth above. Indeed, when the RICC 100 is a triluminal RICC, the catheter tube 102 can include a catheter-tube portion of the primary lumen 112 of the RICC 100, a catheter-tube portion of the secondary lumen 114 of the RICC 100, and a catheter-tube portion of the tertiary lumen 116 of the RICC 100. Before forming the catheter tip 104 coupled to the catheter tube 102 as set forth in the method below, each catheter-tube lumen of the foregoing three catheter-tube lumens 118, 120, and 122 can extend completely through the catheter tube 102. Subsequent to forming the catheter tip 104, however, only the primary catheter-tube lumen 118 typically extends from a proximal end of the catheter tube 102 to a distal end of the catheter tube 102. Indeed, the primary catheter-tube lumen 118 typically extends through both the proximal and distal ends of the catheter tube 102 and continues to extend through the catheter-tip lumen 124 of the catheter tip 104. In contrast, the secondary and tertiary catheter-tube lumens 120 and 122 typically terminate in the distal end portion of the catheter tube 102 by at least some infill of the melted polymeric material of the first polymeric material used to form the catheter tip 104.

The catheter tube 102 can be formed of a second, softer polymeric material than the first polymeric material of the catheter tip 104 set forth below. In other words, the second polymeric material can have a second durometer less than the first durometer of the first polymeric material. Such a second polymeric material can include, but is not limited to, a polyvinyl chloride, a polyethylene, a polyurethane, or a silicone having the second durometer less than the first durometer of the first polymeric material. For example, if the catheter tip 104 is formed of a polyurethane as set forth below, the catheter tube 102 can be formed of a different polyurethane (e.g., a same or different diisocyanate or trii-socyanate reacted with a different diol or triol, a different diisocyanate or triisocyanate reacted with a same or different diol or triol, a same diisocyanate or triisocyanate reacted with a same diol or triol under different conditions or with different additives, etc.) having a second durometer less than a first durometer of the polyurethane of the catheter tip 104. Notably, polyurethanes can be advantageous for the catheter tube 102 in that polyurethanes are relatively stiff at room-temperature but become more pliable in vivo at body temperature, which reduces irritation to blood-vessel walls as well as phlebitis. Polyurethanes are also advantageous in that they can be less thrombogenic than some other polymers. Whether or not the second polymeric material is a polyurethane, the second polymeric material can be configured to be sufficiently stiff ex vivo to impart a column strength to the catheter tube 102 that prevents the catheter tube 102 from collapsing, buckling, or otherwise appreciably deforming when the RICC 100 is advanced into the blood-vessel lumen per the method of placing the RICC 100 set forth below.

Figures 8, 9:
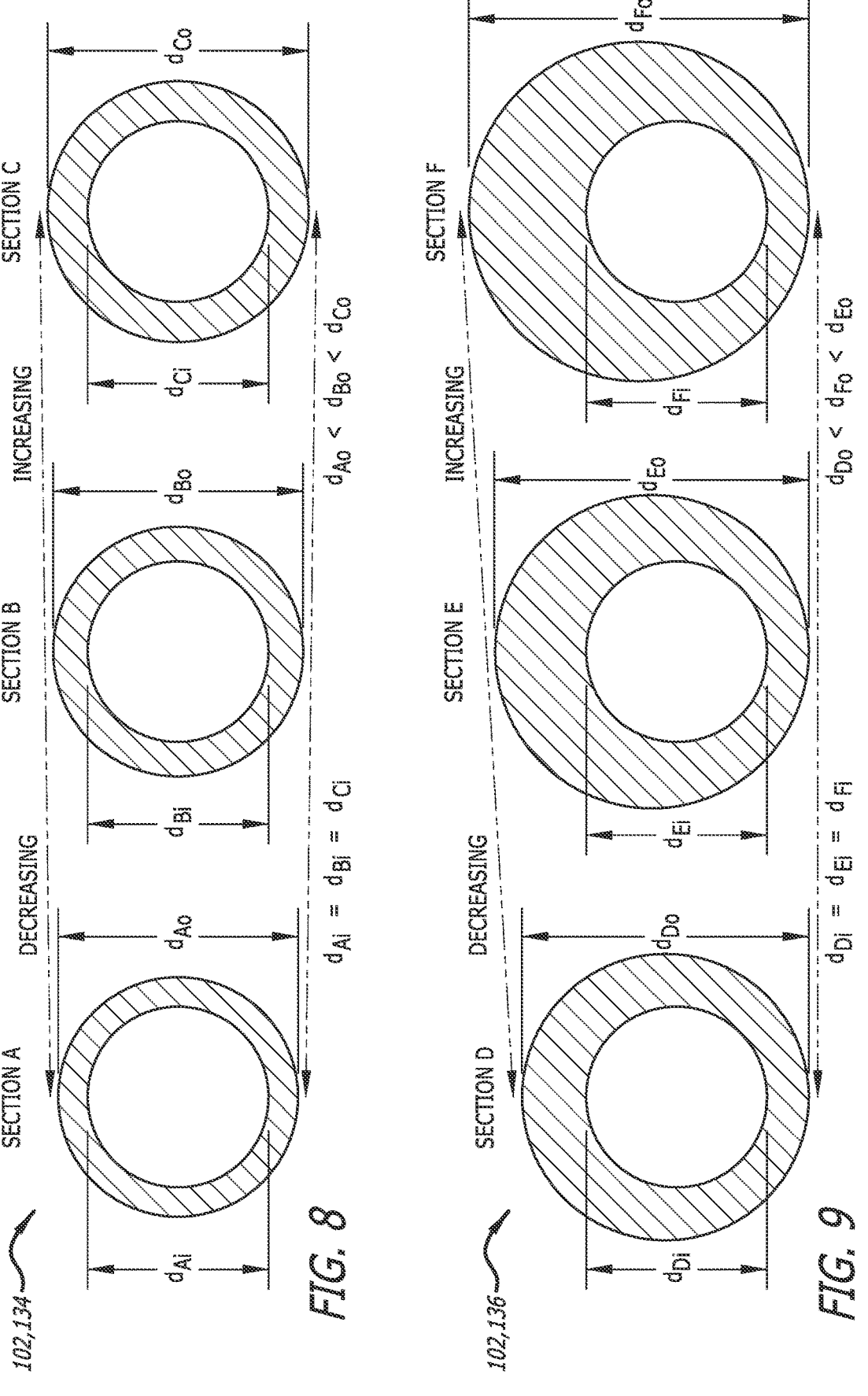
FIG. 8 illustrates transverse cross sections of a second section of the catheter tip of FIG. 2 in accordance with some embodiments.
FIG. 9 illustrates transverse cross sections of a third section of the catheter tip of FIG. 2 in accordance with some embodiments.

FIGS. 2 and 4 illustrate detailed views of the catheter tip 104 coupled to the catheter tube 102 in accordance with some embodiments. FIGS. 3 and 5 illustrate longitudinal cross sections of the catheter tip 104 coupled to the catheter tube 102 of FIGS. 2 and 4, respectively, in accordance with some embodiments. Notably, the catheter tip 104 of FIGS. 2 and 3 and that of FIGS. 4 and 5 are different with respect to their taper profiles as set forth in detail below. FIG. 7 illustrates a detailed view of the catheter tip 104 of FIG. 2 in accordance with some embodiments. FIGS. 8 and 9 illustrate transverse cross sections of the second section 134 of the catheter tip 104 of FIG. 2 and the third section 136 of the catheter tip 104 of FIG. 2, respectively, in accordance with some embodiments.

As shown, the catheter tip 104 can have a first section 132, a second section 134, and a third section 136. The second section 134 of the catheter tip 104 can have a length $l_2$ longer than a length $l_1$ of the first section 132 of the catheter tip 104, and the third section 136 of the catheter tip 104 can have a length $l_3$ longer than the length $l_2$ of the second section 134 of the catheter tip 104. For example, the length $l_2$ of the second section 134 of the catheter tip 104 can be about 4.0 to 5.0 times longer than the length $l_1$ of the first section 132 of the catheter tip 104, and the length $l_3$ of the third section 136 of the catheter tip 104 can be about 4.5 to 7.5 times longer than the length $l_2$ of the second section 134 of the catheter tip 104. However, it should be understood relative lengths disclosed herein such as those of the first, second, and third sections 132, 134, and 136 of the catheter tip 104, as well as dimensions disclosed herein, generally relate to a 6-8 Fr RICC such as a 7 Fr RICC. The relative lengths and dimensions for larger RICCS (e.g., 7-14 Fr) or smaller RICCs (e.g., 4-6 Fr) as measured on the French catheter scale can vary, optionally, proportionally, by which the relative lengths and dimensions for the larger RICCs and smaller RICCs are also disclosed.

Beginning with the first section 132 of the catheter tip 104, the first section 132 can have a uniform taper having a constant first taper angle over an outer diameter thereof configured for immediately dilating tissue around a needle tract formed with an introducer needle as the RICC 100 is advanced into a blood-vessel lumen of a patient per the method of placing the RICC 100 set forth below. The first taper angle can be about 15.0-45.0°, including about 15.0-35.0°, such as about 25.0-35.0°, or, for example, about 30.0°, inclusive or exclusive of any range endpoints. The uniform taper of the first section 132 of the catheter tip 104 can dilate the tissue around the needle tract from a size commensurate with an outer diameter of a needle shaft of the introducer needle to a size commensurate with the outer diameter of the second section 134 of the catheter tip 104, at its least. Being that the uniform taper of the first section 132 of the catheter tube 102 is not blunt like a catheter tip of a typical ACVC, the first section 132 of the catheter tip 104 can reduce the force needed to insert the RICC 100 into the needle tract over that of the typical ACVC.

Each successive transverse cross section of the first section 132 of the catheter tip 104 can approximate a larger concentric annulus in a proximal direction along the first section 132 of the catheter tip 104. In addition, each successive transverse cross section of the first section 132 of the catheter tip 104 can approximate a smaller concentric annulus in a distal direction along the first section 132 of the catheter tip 104. Each concentric annulus of the foregoing larger and smaller concentric annuli can be defined by the outer diameter of the first section 132 of the catheter tip 104 and the inner diameter of the catheter-tube portion of the primary lumen 112 of the RICC 100, thereby providing the uniform taper of the first section 132 of the catheter tip 104. While the foregoing is not shown for the first section 132 of the catheter tip 104, it is analogously shown in FIGS. 7 and 8 for the second section 134 of the catheter tip 104 in embodiments in which the second section 134 has its uniform taper.

Continuing with the second section 134 of the catheter tip 104, the second section 134 can have a uniform taper having a constant second taper angle over an outer diameter thereof as shown in FIGS. 2, 3, and 8. (See FIG. 8, wherein the outer diameter of the second section 134 of the catheter tip 104 is indicated by $d_{Ao}$, $d_{Bo}$, and $d_{Co}$.) Alternatively, the outer diameter of the second section 134 of the catheter tip 104 can be consistent along the second section 134 without the uniform taper as shown in FIGS. 4 and 5. When the second section 134 of the catheter tip 104 has the uniform taper, the second taper angle can be less than or equal to about 10.0°, including less than or equal to about 5.0°, such as less than or equal to about 2.5°, for example, less than or equal to about 1.0°. Such a uniform taper can be configured for immediately further dilating the tissue around the needle tract as the RICC 100 is advanced into the blood-vessel lumen of the patient per the method of placing the RICC 100 set forth below. The uniform taper of the second section 134 of the catheter tip 104 can dilate the tissue around the needle tract from a size commensurate with the outer diameter of the first section 132 of the catheter tip 104, at its greatest, to a size commensurate with the outer diameter of the third section 136 of the catheter tip 104, at its least. Further being that the uniform taper of the second section 134 of the catheter tube 102 is not blunt like the catheter tip of the typical ACVC, the second section 134 of the catheter tip 104 can further reduce the force needed to insert the RICC 100 into the needle tract over that of the typical ACVC.

As shown in FIGS. 7 and 8, each successive transverse cross section of the second section 134 of the catheter tip 104 can approximate a larger concentric annulus in the proximal direction along the second section 134 of the catheter tip 104. In addition, each successive transverse cross section of the second section 134 of the catheter tip 104 can approximate a smaller concentric annulus in the distal direction along the second section 134 of the catheter tip 104. Each concentric annulus of the foregoing larger and smaller concentric annuli can be defined by the outer diameter (e.g., $d_{Ao}$, $d_{Bo}$, or $d_{Co}$) of the second section 134 of the catheter tip 104 and the inner diameter (e.g., $d_{Ai}$, $d_{Bi}$, or $d_{Ci}$) of the catheter-tube portion of the primary lumen 112 of the RICC 100, thereby providing the uniform taper of the second section 134 of the catheter tip 104.

As to the third section 136 of the catheter tip 104, the third section 136 can have a non-uniform taper having a variable third taper angle over an outer diameter thereof as shown in FIGS. 2, 3, and 9. (See FIG. 9, wherein the outer diameter of the third section 136 of the catheter tip 104 is indicated by $d_{Do}$, $d_{Eo}$, and $d_{Fo}$.) Such a non-uniform taper can be configured for immediately further dilating the tissue around the needle tract as the RICC 100 is advanced into the blood-vessel lumen of the patient per method of placing the RICC 100 set forth below. The non-uniform taper of the third section 136 of the catheter tip 104 can dilate the tissue around the needle tract from the size commensurate with the outer diameter of the second section 134 of the catheter tip 104, at its greatest, to a size commensurate with an outer diameter of the catheter tube 102. Further being that the non-uniform taper of the third section 136 of the catheter tube 102 is not blunt like the catheter tip of the typical ACVC, the third section 136 of the catheter tip 104 can further reduce the force needed to insert the RICC 100 into the needle tract over that of the typical ACVC. Indeed, the third section 136 of the catheter tip 104 is configured to integrate into the catheter tip 104 dilation normally done by a dilator in the Seldinger technique, thereby reducing the force needed to insert the RICC 100 into the needle tract and eliminating a separate dilation step.

As shown in FIGS. 7 and 9, each successive transverse cross section of the third section 136 of the catheter tip 104 can approximate a larger eccentric annulus in the proximal direction along the third section 136 of the catheter tip 104. In addition, each successive transverse cross section of the third section 136 of the catheter tip 104 can approximate a smaller eccentric annulus in the distal direction along the third section 136 of the catheter tip 104. Each eccentric annulus of the foregoing larger and smaller eccentric annuli can be defined by the outer diameter (e.g., $d_{Do}$, $d_{Eo}$, or $d_{Fo}$) of the third section 136 of the catheter tip 104 and the inner diameter (e.g., $d_{Di}$, $d_{Ei}$, or $d_{Fi}$) of the catheter-tube portion of the primary lumen 112 of the RICC 100, thereby providing the non-uniform taper of the third section 136 of the catheter tip 104.

As set forth above, the uniform taper of the first section 132 of the catheter tip 104 can have the constant first taper angle, the uniform taper of the second section 134 of the catheter tip 104 can, when present, have the constant second taper angle, and the non-uniform taper of the third section 136 of the catheter tip 104 can have the variable third taper angle. As shown in FIGS. 2 and 3 and FIGS. 4 and 5, the first taper angle can be greater than the third taper angle at a greatest taper angle of the third taper angle. That, and the third taper angle can be greater than the second taper angle at the greatest taper angle of the third taper angle, which third taper angle being associated with the non-uniform taper of the third section 136 of the catheter tip 104 can vary up from about 0.0° as set forth below.

Notably, the third taper angle of the non-uniform taper of the third section 136 of the catheter tip 104 can be non-uniform in at least two different ways. Consider, for example, an abluminal surface of the third section 136 of the catheter tip 104 ruled such that every point on the abluminal surface is on a longitudinal surface line coplanar with a central axis of the catheter-tip lumen 124 of the catheter tip 104. The third taper angle can be non-uniform in that a bottommost surface line 138 coincident with a bottom edge of a bilaterally symmetric, longitudinal cross section of the third section 136 of the catheter tip 104 such as that shown in FIG. 3 can have a different taper angle than that of a topmost surface line 140 coincident with a top edge of the bilaterally symmetric, longitudinal cross section of the third section 136 of the catheter tip 104 such as that also shown in FIG. 3. Indeed, the bottommost surface line 138 can have the least taper angle (e.g., about 0.0°) and the topmost surface line 140 can have the greatest taper angle, which can be less than or equal to about 15.0°, including less than or equal to about 10.0°, such as less than or equal to about 7.5°, for example, less than or equal to about 5.0°. The third taper angle can be further non-uniform in that the bottommost surface line 138 such as that shown in FIG. 5 can be linear and the topmost surface line 140 such as that also shown in FIG. 5 can be non-linear such as gently sigmoidal. Surface lines on the abluminal surface of the third section 136 of the catheter tip 104 between the bottommost and topmost surface lines 138 and 140 can be increasingly non-liner such as increasingly sigmoidal with an entirety of the bottommost surface line 138 having the least taper angle (e.g., about 0.0°) and the topmost surface line 140 having a medial portion achieving the greatest taper angle, which can be less than or equal to about 15.0°, including less than or equal to about 10.0°, such as less than or equal to about 7.5°, for example, less than or equal to about 5.0°.

The catheter tip 104 can be formed of a first, harder polymeric material than the second polymeric material of the catheter tube 102 set forth above. In other words, the first polymeric material can have a first durometer greater than the second durometer of the second polymeric material. The first durometer can be a Shore A durometer of about 70-100, including a Shore A durometer of about 80-100, such as a Shore A durometer of about 90-100, for example, a Shore durometer of about 90-95. Such a first polymeric material can include, but is not limited to, a polytetrafluoroethylene, a polypropylene, or a polyurethane having the first durometer greater than the second durometer of the second polymeric material. For example, the catheter tip 104 can be formed of a polyurethane having the first durometer. Like that set forth above with respect to the catheter tube 102, polyurethanes can also be advantageous for the catheter tip 104. Whether or not the first polymeric material is a polyurethane, the first polymeric material can be configured to be sufficiently pliable in vivo at body temperature to prevent trauma to a blood-vessel lumen of a patient when the RICC 100 is advanced into the blood-vessel lumen per the method of placing the RICC 100 set forth below. However, the first polymeric material can be configured to soften less than the second polymeric material in vivo at body temperature, in a presence of moisture, or both. Indeed, the first polymeric material can be configured to remain sufficiently stiff to prevent the catheter tip 104 from collapsing, buckling, or otherwise appreciably deforming when the RICC 100 is advanced into the blood-vessel lumen of the patient. Additionally or alternatively, the first polymeric material can be configured to remain sufficiently stiff to prevent the catheter-tip lumen 124 of the catheter tip 104 from collapsing when aspirating through the catheter tip 104.

It should be understood that the first durometer of the first polymeric material and the second durometer of the second polymeric material can be on different hardness scales (e.g., Type A or Type D). With this understanding, the second durometer of the second polymeric material might not be numerically less than the first durometer of the first polymeric material when the second durometer is less than the first durometer. Indeed, the hardness of the second polymeric material can still be less than the hardness of the first polymeric material as the different hardness scales—each of which ranges from 0 to 100—are designed for characterizing different materials in groups of the materials having a like hardness.

The catheter hub 106 can include one or more catheter-hub lumens corresponding in number to the one-or-more catheter-tube lumens such as the three catheter-hub lumens set forth above, which correspond in number to the three catheter-tube lumens 118, 120, and 122 also set forth above. When the RICC 100 is a triluminal RICC, the catheter hub 106 can include a catheter-hub portion of the primary lumen 112 of the RICC 100, a catheter-hub portion of the secondary lumen 114 of the RICC 100, and a catheter-hub portion of the tertiary lumen 116 of the RICC 100. The one-or-more catheter-hub lumens can extend through an entirety of the catheter hub 106 from a proximal end of the catheter hub 106 to a distal end of the catheter hub 106.

The one-or-more extension legs 108 can respectively include one or more extension-leg lumens, which, in turn, correspond in number to the one-or-more catheter-hub lumens such as the three extension-leg lumens set forth above, which correspond in number to the three catheter-hub lumens also set forth above. When the RICC 100 is a triluminal RICC, the one-or-more extension legs 108 can include a primary extension leg including an extension-leg portion of the primary lumen 112 of the RICC 100, a secondary extension leg including an extension-leg portion of the secondary lumen 114 of the RICC 100, and a tertiary extension leg including an extension-leg portion of the tertiary lumen 116 of the RICC 100. Each extension-leg lumen of the one-or-more extension-leg lumens can extend through an entirety of its corresponding extension leg from a proximal end of the extension leg to a distal end of the extension leg.

Notably, any component of the RICC 100 selected from the catheter tip 104, the catheter tube 102, the catheter hub 106, the one-or-more extension legs 108, and the one-or-more extension-leg connectors 110 can include an antimicrobial thereon or therein. In an example, the catheter tube 102 and the catheter tip 104 coupled thereto can include an antimicrobial coating on the abluminal surfaces of the catheter tip 104 and the catheter tube 102. In another example, a pre-extrusion material of the catheter tube 102 can include the antimicrobial admixed therein such that the antimicrobial is incorporated into the catheter tube 102 when extruded, the antimicrobial protecting both the abluminal surface of the catheter tube 102 and the luminal surface of the catheter tube 102 from microbial contamination. Additionally or alternatively, the polymeric plug 150 of the first polymeric material can include the antimicrobial admixed therein such that the antimicrobial is incorporated into the catheter tip 104 when formed as set forth below, the antimicrobial protecting both the abluminal surface of the catheter tip 104 and the luminal surface of the catheter tip 104 from microbial contamination.

Methods

Methods include at least methods of forming the catheter tip 104 of the RICC 100 as well as placing such a RICC in a blood-vessel lumen of a patient.

Figure 10:
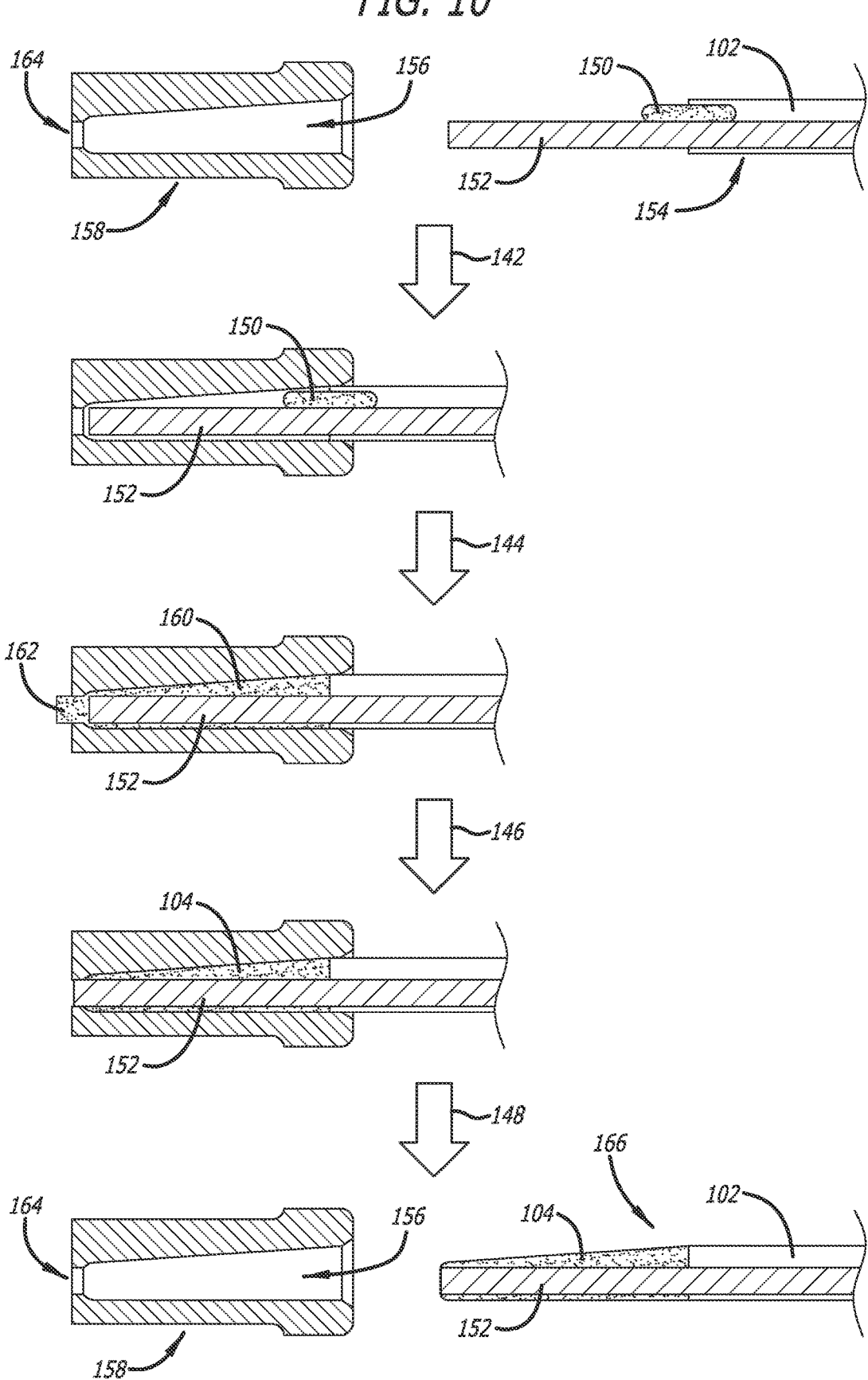
FIG. 10 illustrates a method for forming the catheter tip of either FIG. 2 or FIG. 4 in accordance with some embodiments.

FIG. 10 illustrates a method for forming the catheter tip 104 of either FIG. 2 or FIG. 4 in accordance with some embodiments.

A method for forming the catheter tip 104 of the RICC 100 can include one or more steps selected from a catheter tube-obtaining step, a polymeric plug-inserting step, a catheter tube-mounting step, a workpiece-inserting step 142, a die-heating step 144, a mandrel-thrusting step 146, a workpiece-removing step 148, and a mandrel-removing step.

The catheter tube-obtaining step can include either sourcing or extruding the catheter tube 102 of the second polymeric material, the second polymeric material being softer than the first polymer material of the catheter tip 104 as set forth above. Again, the catheter tube 102 can include the primary catheter-tube lumen 118, the secondary catheter-tube lumen 120, and the tertiary catheter-tube lumen 122 corresponding to catheter-tube portions of the primary lumen 112, the secondary lumen 114, and the tertiary lumen 116 of the RICC 100, respectively.

The polymeric plug-inserting step can include at least partially inserting a polymeric plug 150 of the first polymeric material into each lumen of the secondary and tertiary catheter-tube lumens 120 and 122 for melting the first polymeric material in the cavity 156 of the RF-welding die 158 while heating the RF-welding die 158 in the die-heating step 144 set forth below.

The catheter tube-mounting step can include mounting the catheter tube 102 on a straight mandrel 152 to form a mandrel-mounted catheter tube 154 for a workpiece, optionally, with the polymeric plug 150 of the first polymeric material inserted into each lumen of the secondary and tertiary catheter-tube lumens 120 and 122, as the catheter tube-mounting step can be performed either before or after the polymeric plug-inserting step.

The workpiece-inserting step 142 can include inserting the mandrel-mounted catheter tube 154 into a cavity 156 of an RF-welding die 158. A distal end of the mandrel 152 of the mandrel-mounted catheter tube 154 can remain short of an end of the cavity 156 after the inserting of the mandrel-mounted catheter tube 154 into the cavity 156.

The die-heating step 144 can include heating the RF-welding die 158 to melt the first polymeric material of the polymeric plug 150 extending from each lumen of the secondary and tertiary catheter-tube lumens 120 and 122 in the cavity 156 of the RF-welding die 158. During the heating of the RF-welding die 158, molten polymeric material of the first polymeric material can be allowed to conform to the cavity 156 around a distal portion of the mandrel 152 to form, in a single piece, a nascent catheter tip 160 coupled to the distal end portion of the catheter tube 102.

The mandrel-thrusting step 146 can include thrusting the distal end of the mandrel 152 into the end of the cavity 156 of the RF-welding die 158 when molten exudate 162 of the molten polymeric material exudes through an exit hole 164 in the end of the cavity 156. Excess polymeric material can be cut from a distal end of the nascent catheter tip 160 with the thrusting of the distal end of the mandrel 152 into the end of the cavity 156 to provide a mandrel-mounted tipped catheter tube 166 for the workpiece, a tipped catheter tube thereof including the catheter tip 104 coupled to the distal end portion of the catheter tube 102.

The workpiece-removing step 148 can include removing the mandrel-mounted tipped catheter tube 166 from the cavity 156 of the RF-welding die 158. Notably, a remainder of the polymeric plug 150 in the secondary and tertiary catheter-tube lumens 120 and 122, melted polymeric material of the first polymeric material in the secondary and tertiary catheter-tube lumens 120 and 122, or a combination thereof in the secondary and tertiary catheter-tube lumens 120 and 122 terminate or close off the secondary and tertiary catheter-tube lumens 120 and 122 as infill upon cooling the mandrel-mounted tipped catheter tube 166 or, after the mandrel-removing step set forth below, the tipped catheter tube thereof.

The mandrel-removing step can include removing the mandrel 152 from the mandrel-mounted tipped catheter tube 166 to clear a primary lumen of the tipped catheter tube of the mandrel 152, thereby providing the tipped catheter tube.

Notably, due to forming the catheter tip 104 of the RICC 100 in accordance with the foregoing method, the abluminal surface of the third section 136 of the catheter tip 104 can smoothly transition to the abluminal surface of the catheter tube 102 without edges that catch on the skin of the patient when the when the RICC 100 is advanced into the blood-vessel lumen per the method of placing the RICC 100 set forth below.

While not shown, a method of placing the RICC 100 having the catheter tip 104 can include one or more steps selected from a needle tract-establishing step, an access guidewire-advancing step, an introducer needle-withdrawing step, an initial RICC-advancing step including a dilating step or operation performed simultaneously therewith, a guidewire-exchanging step including an access guidewire-withdrawing step and an initial maneuver guidewire-advancing step, a subsequent maneuver guidewire-advancing step, a subsequent RICC-advancing step, and a maneuver guidewire-withdrawing step.

The needle tract-establishing step can include establishing a needle tract from an area of skin to a blood-vessel lumen of a patient with an introducer needle.

The access guidewire-advancing step can include advancing a distal portion of an access guidewire into the blood-vessel lumen through the introducer needle until access to the blood-vessel lumen is secured with the access guidewire.

The introducer needle-withdrawing step can include withdrawing the introducer needle from the blood-vessel lumen leaving the access guidewire in place in the blood-vessel lumen.

The initial RICC-advancing step can include advancing a distal portion of the RICC 100 over the access guidewire into the blood-vessel lumen until access to the blood-vessel lumen is secured with the catheter tube 102. Neither the skin nor the tissue around the needle tract catches between an outer diameter of the access guidewire and an inner diameter of the catheter tip 104 due to tight control of manufacturing tolerance between the foregoing diameters. As set forth above, the distal portion of the RICC 100 can include the catheter tip 104 of the first polymeric material having the first section 132, the second section 134, and the third section 136 coupled to the distal end portion of the catheter tube 102 of the second polymeric material. The first polymeric material of the catheter tip 104 can be configured to remain sufficiently stiff to prevent the catheter tip 104 from collapsing, buckling, or otherwise appreciably deforming while advancing the distal portion of the RICC 100 over the access guidewire into the blood-vessel lumen in accordance with the initial RICC-advancing step.

The dilating step or operation can include dilating tissue around the needle tract leading to the blood-vessel lumen while advancing the distal portion of the RICC 100 over the access guidewire into the blood-vessel lumen in accordance with the initial RICC-advancing step. As such, the dilating step or operation is part of the initial RICC-advancing step—not a separate step or operation therefrom like that needed with the Seldinger technique. As set forth above, the first section 132 of the catheter tip 104 can have the uniform taper over the outer diameter of the first section 132 configured for immediately dilating the tissue from the size commensurate with the outer diameter of the needle shaft of the introducer needle to the size commensurate with the outer diameter of the second section 134 of the catheter tip 104. The third section 136 of the catheter tip 104 have the non-uniform taper over the outer diameter of the third section 136 configured for immediately dilating the tissue from the size commensurate with the outer diameter of the second section 134 of the catheter tip 104 to the size commensurate with the outer diameter of the catheter tube 102.

The exchanging step can include exchanging the access guidewire with a maneuver guidewire, which, in turn, can include the access guidewire-withdrawing step and the initial maneuver guidewire-advancing step. The access guidewire-withdrawing step can include withdrawing the access guidewire from the blood-vessel lumen leaving the catheter tube 102 in place in the blood-vessel lumen. The initial maneuver guidewire-advancing step can include advancing a distal portion of the maneuver guidewire into the blood-vessel lumen.

The subsequent maneuver guidewire-advancing step can include advancing the distal portion of the maneuver guidewire farther into the blood-vessel lumen to a lower ⅓ of a superior vena cava ("SVC") of a heart of the patient.

The subsequent RICC-advancing step can include advancing the distal portion of the RICC 100 farther into the blood-vessel lumen over the maneuver guidewire to the lower ⅓ of the SVC. Notably, the first polymeric material is also sufficiently pliable to prevent trauma to the blood-vessel lumen while advancing the distal portion of the RICC 100 over the maneuver guidewire farther into the blood-vessel lumen in accordance with the subsequent RICC-advancing step.

The maneuver guidewire-withdrawing step can include withdrawing the maneuver guidewire leaving the catheter tube 102 in place in the lower ⅓ of the SVC.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A rapidly insertable central catheter ("RICC"), comprising:

a catheter tube including a catheter-tube portion of a primary lumen of the RICC having an inner diameter;

a single-piece catheter tip coupled to a distal end portion of the catheter tube having a first section, a second section, and a third section, wherein:

the first section of the catheter tip has a uniform taper over an outer diameter of the first section for dilating tissue around a needle tract from a size commensurate with an outer diameter of a needle shaft of an introducer needle to a size commensurate with an outer diameter of the second section of the catheter tip;

the second section of the catheter tip has a uniform taper for dilating the tissue from a size commensurate with the outer diameter of the first section of the catheter tip to a size commensurate with an outer diameter of the third section of the catheter tip, each successive transverse cross section of the second section of the catheter tip approximating a larger concentric annulus in a proximal direction along the second section of the catheter tip and a smaller concentric annulus in a distal direction along the second section of the catheter tip, and each concentric annulus of the larger concentric annulus and the smaller concentric annulus defined by the outer diameter of the second section of the catheter tip and the inner diameter of the catheter-tube portion of the primary lumen of the RICC, thereby providing the uniform taper of the second section of the catheter tip; and the third section of the catheter tip has a non-uniform taper over the outer diameter of the third section for dilating the tissue from the size commensurate with the outer diameter of the second section of the catheter tip to a size commensurate with an outer diameter of the catheter tube;

a catheter hub coupled to a proximal portion of the catheter tube; and one or more extension legs, each extension leg of the one or more extension legs coupled to the catheter hub by a distal portion thereof.

2. The RICC of claim 1, wherein each successive transverse cross section of the first section of the catheter tip approximates a larger concentric annulus in a proximal direction along the first section of the catheter tip and a smaller concentric annulus in a distal direction along the first section of the catheter tip, each concentric annulus of the larger concentric annulus and the smaller concentric annulus defined by the outer diameter of the first section of the catheter tip and the inner diameter of the catheter-tube portion of the primary lumen of the RICC, thereby providing the uniform taper of the first section of the catheter tip.

3. The RICC of claim 1, wherein each successive transverse cross section of the third section of the catheter tip approximates a larger eccentric annulus in a proximal direction along the third section of the catheter tip and a smaller eccentric annulus in a distal direction along the third section of the catheter tip, each eccentric annulus of the larger concentric annulus and smaller eccentric annulus defined by the outer diameter of the third section of the catheter tip and the inner diameter of the catheter-tube portion of the primary lumen of the RICC, thereby providing the non-uniform taper of the third section of the catheter tip.

4. The RICC of claim 1, wherein the uniform taper of the first section of the catheter tip has a constant first taper angle and the non-uniform taper of the third section of the catheter tip has a variable third taper angle, the constant first taper angle greater than the variable third taper angle at a greatest taper angle of the variable third taper angle.

5. The RICC of claim 1, wherein the uniform taper of the first section of the catheter tip has a constant first taper angle, the uniform taper of the second section of the catheter tip has a constant second taper angle, and the non-uniform taper of the third section of the catheter tip has a variable third taper angle, the constant first taper angle greater than the variable third taper angle at a greatest taper angle of the variable third taper angle, and the variable third taper angle greater than the constant second taper angle at the greatest taper angle of the variable third taper angle.

6. The RICC of claim 1, wherein the second section of the catheter tip is about 4.0 to 5.0 times longer than the first section of the catheter tip.

7. The RICC of claim 1, wherein the third section of the catheter tip is about 4.5 to 7.5 times longer than the second section of the catheter tip.

8. The RICC of claim 1, wherein the catheter tip is of a first polymeric material and the catheter tube is of a second, softer polymeric material.

9. The RICC of claim 8, wherein the first polymeric material is sufficiently stiff to prevent the catheter tip from collapsing, buckling, or otherwise appreciably deforming when a distal portion of the RICC is advanced into a blood-vessel lumen of a patient, the first polymeric material also being sufficiently pliable to prevent trauma to the blood-vessel lumen when the distal portion of the RICC is advanced farther into the blood-vessel lumen.

10. The RICC of claim 8, wherein the RICC includes a set of three lumens including the primary lumen, a secondary lumen, and a tertiary lumen formed of fluidly connected portions of at least three catheter-tube lumens, three catheter-hub lumens, and three extension-leg lumens, the secondary lumen and the tertiary lumen terminating in the distal end portion of the catheter tube by at least some infill of melted polymeric material of the first polymeric material.

11. The RICC of claim 10, wherein the primary lumen has a primary-lumen aperture in a distal end of the catheter tip, the secondary lumen has a secondary-lumen aperture in a side of the distal portion of the catheter tube, and the tertiary lumen has a tertiary-lumen aperture in the side of the distal end portion of the catheter tube but proximal of the secondary-lumen aperture.

12. A method for forming a catheter tip of a rapidly insertable central catheter ("RICC"), comprising:

inserting a mandrel-mounted catheter tube into a cavity of a radiofrequency ("RF")-welding die, a distal end of a mandrel of the mandrel-mounted catheter tube being short of an end of the cavity after inserting the mandrel-mounted catheter tube therein;

heating the RF-welding die to melt a first polymeric material in the cavity of the RF-welding die, molten polymeric material of the first polymeric material allowed to conform to the cavity around the mandrel during the heating of the RF-welding die to form, in a single piece, a nascent catheter tip coupled to a distal end portion of the catheter tube;

thrusting the distal end of the mandrel into the end of the cavity of the RF-welding die when the molten polymeric material exudes through an exit hole in the end of the cavity, excess polymeric material being cut from a distal end of the nascent catheter tip to form the catheter tip coupled to the distal end portion of the catheter tube with thrusting the distal end of the mandrel into the end of the cavity, wherein:

a first section of the catheter tip has a uniform taper over an outer diameter of the first section for dilating tissue around a needle tract from a size commensurate with an outer diameter of a needle shaft of an introducer needle to a size commensurate with an outer diameter of a second section of the catheter tip;

the second section of the catheter tip has a uniform taper for dilating the tissue from a size commensurate with the outer diameter of the first section of the catheter tip to a size commensurate with an outer diameter of a third section of the catheter tip, each successive transverse cross section of the second section of the catheter tip approximating a larger concentric annulus in a proximal direction along the second section of the catheter tip and a smaller concentric annulus in a distal direction along the second section of the catheter tip, and each concentric annulus of the larger concentric annulus and the smaller concentric annulus defined by the outer diameter of the second section of the catheter tip and an inner diameter of a catheter-tube portion of a primary lumen of the RICC, thereby providing the uniform taper of the second section of the catheter tip; and a third section of the catheter tip has a non-uniform taper over the outer diameter of the third section for dilating the tissue from the size commensurate with the outer diameter of the second section of the catheter tip to a size commensurate with an outer diameter of the catheter tube.

13. The method of claim 12, further comprising:

sourcing or extruding the catheter tube of a second polymeric material softer than the first polymeric material, the catheter tube including a primary catheter-tube lumen, a secondary catheter-tube lumen, and a tertiary catheter-tube lumen corresponding to catheter-tube portions of a primary lumen, a secondary lumen, and a tertiary lumen of the RICC, respectively.

14. The method of claim 12, wherein the first polymeric material of the catheter tip is sufficiently stiff to prevent the catheter tip from collapsing, buckling, or otherwise appreciably deforming when a distal portion of the RICC is advanced into a blood-vessel lumen of a patient, the first polymeric material of the catheter tip also being sufficiently pliable to prevent trauma to the blood-vessel lumen when the distal portion of the RICC is advanced farther into the blood-vessel lumen.

15. A method of placing a rapidly insertable central catheter ("RICC"), comprising:

advancing a distal portion of the RICC over an access guidewire into a blood-vessel lumen of a patient, the distal portion of the RICC including a single-piece catheter tip of a first polymeric material having a first section, a second section, and a third section coupled to a distal end portion of a catheter tube of a second polymeric material, the first polymeric material of the catheter tip being sufficiently stiff to prevent the catheter tip from collapsing, buckling, or otherwise appreciably deforming while advancing the distal portion of the RICC over the access guidewire into the blood-vessel lumen; and dilating tissue around a needle tract leading to the blood-vessel lumen while advancing the distal portion of the RICC into the blood-vessel lumen, wherein:

the first section of the catheter tip has a uniform taper over an outer diameter of the first section for dilating the tissue from a size commensurate with an outer diameter of a needle shaft of an introducer needle used to establish the needle tract to a size commensurate with an outer diameter of the second section of the catheter tip;

a second section of the catheter tip has a uniform taper for dilating the tissue from a size commensurate with the outer diameter of the first section of the catheter tip to a size commensurate with an outer diameter of the third section of the catheter tip, each successive transverse cross section of the second section of the catheter tip approximating a larger concentric annulus in a proximal direction along the second section of the catheter tip and a smaller concentric annulus in a distal direction along the second section of the catheter tip, and each concentric annulus of the larger concentric annulus and the smaller concentric annulus defined by the outer diameter of the second section of the catheter tip and an inner diameter of a catheter-tube portion of a primary lumen of the RICC, thereby providing the uniform taper of the second section of the catheter tip; and the third section of the catheter tip having a non-uniform taper over the outer diameter of the third section for dilating the tissue from the size commensurate with the outer diameter of the second section of the catheter tip to a size commensurate with an outer diameter of the catheter tube.

16. The method of claim 15, further comprising:

exchanging the access guidewire with a maneuver guidewire;

advancing a distal portion of the maneuver guidewire farther into the blood-vessel lumen to a lower ⅓ of a superior vena cava ("SVC") of a heart of the patient;

advancing the distal portion of the RICC farther into the blood-vessel lumen over the maneuver guidewire to the lower ⅓ of the SVC, the first polymeric material also being sufficiently pliable to prevent trauma to the blood-vessel lumen while advancing the distal portion of the RICC over the maneuver guidewire farther into the blood-vessel lumen; and withdrawing the maneuver guidewire leaving the catheter tube in place in the lower ⅓ of the SVC.

* * * * *